United States Patent [19]

Young et al.

[11] Patent Number: 5,507,426
[45] Date of Patent: Apr. 16, 1996

[54] APPARATUS FOR APPLYING SURGICAL FASTENERS

[75] Inventors: Wayne P. Young, Brewster, N.Y.; Daniel E. Alesi, Sherman; Kenneth E. Toso, Wilton, both of Conn.

[73] Assignee: United States Surgical Corporation, Norwalk, Conn.

[21] Appl. No.: 286,851

[22] Filed: Aug. 5, 1994

[51] Int. Cl.⁶ .................................................. A61B 17/068
[52] U.S. Cl. ...................... 227/180.1; 227/19; 227/181.1; 227/176.1
[58] Field of Search ..................................... 227/175, 176, 227/178, 179, 181, 19

[56] References Cited

U.S. PATENT DOCUMENTS

| | | |
|---|---|---|
| 4,520,817 | 6/1985 | Green . |
| 4,605,001 | 8/1986 | Rothfuss et al. . |
| 4,610,383 | 9/1986 | Rothfuss et al. . |
| 4,784,137 | 11/1988 | Kulik et al. . |
| 5,040,715 | 8/1991 | Green et al. . |
| 5,065,929 | 11/1991 | Schulze et al. . |
| 5,071,430 | 12/1991 | de Salis et al. . |
| 5,307,976 | 5/1994 | Olson et al. ............................... 227/19 |
| 5,312,023 | 5/1994 | Green et al. . |
| 5,318,221 | 6/1994 | Green et al. . |
| 5,326,013 | 7/1994 | Green et al. ............................... 227/19 |
| 5,346,115 | 9/1994 | Perouse et al. ............................ 227/19 |
| 5,433,721 | 7/1995 | Hooven et al. . |

FOREIGN PATENT DOCUMENTS 51-149985  5/1950  Japan .

*Primary Examiner*—Scott A. Smith

[57] ABSTRACT

An apparatus is provided for applying surgical fasteners to body tissue. The apparatus has a handle assembly and an elongated body which extends distally from the handle assembly. A fastener applying assembly is operatively associated with a distal end of the elongated body and includes a cartridge housing a plurality of staples and an anvil movable between an open position and a closed position. An actuation assembly is configured to translate through the fastener applying assembly to effect progressive closure of the anvil and concomitantly effect sequential ejection of staples from the cartridge.

28 Claims, 7 Drawing Sheets

APPARATUS FOR APPLYING SURGICAL FASTENERS

BACKGROUND

1. Technical Field

The apparatus relates to a surgical stapling apparatus, and more particularly, to an apparatus for sequentially applying a plurality of surgical fasteners to body tissue and optionally incising the fastened tissue.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a disposable cartridge which houses a plurality of staples arranged in at least two lateral rows while the other member comprises an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. Nos. 3,079,606 and 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. No. 4,429,695.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in U.S. Pat. Nos. 5,040,715; 5,312,023; 5,318,221; and 5,326,013. In general, these instruments are provided with clamping structure to effect approximation of an anvil and a cartridge to secure tissue therebetween, and staple firing structure to effect sequential ejection of a plurality of fasteners from the cartridge after the tissue has been secured. It would be beneficial however, to provide an endoscopic stapling device having actuation structure configured to effect progressive approximation of an anvil and a cartridge concomitant with the sequential ejection of a plurality of fasteners from the cartridge.

SUMMARY

A surgical apparatus for effecting the sequential application of a plurality of surgical fasteners to body tissue is provided. The apparatus includes a handle portion, a body portion extending from the handle portion, a cartridge housing supported at a distal end portion of the body portion and containing a plurality of surgical fasteners and defining a tissue contacting surface, and an anvil member defining a fastener forming surface against which fasteners ejected from the cartridge assembly are driven.

The anvil member is mounted at a location spaced from the handle portion and is movable between a first position wherein the fastener forming surface is spaced from the tissue contacting surface and a closed position wherein the fastener forming surface and the tissue contacting surface are in closer cooperative alignment. The apparatus further includes an actuator which is configured to progressively move the anvil member from the open position to the closed position and concomitantly eject a plurality of surgical fasteners from the cartridge to be formed against the anvil. A drive mechanism is provided to drive the actuator. The drive mechanism is operable from the handle portion and extends through the body portion to the anvil member.

In a preferred embodiment of the surgical apparatus, the cartridge housing and the anvil member each have a corresponding longitudinally extending slot formed therein for accommodating the translation of the actuator. The actuator preferably includes an upper cam beam, a transverse central portion, and a lower support beam parallel to the upper cam beam. A plurality of spaced apart cam plates are provided on the actuator and are configured to engage a plurality of staple pushers disposed within the cartridge housing to effect the ejection of surgical fasteners therefrom.

In one embodiment, a cutting blade is mounted on the actuator for incising stapled tissue as the actuator translates through the fastener applying assembly. The cutting blade is preferably formed on a leading edge of the central portion of the actuator.

In one embodiment, the drive mechanism includes a pneumatic drive system having a canister of compressed fluid disposed within the handle portion, a longitudinally extending piston chamber defined in the handle portion, a piston configured to translate through the piston chamber, and a drive shaft extending from the piston to the actuator. A trigger mechanism is preferably associated with the pneumatic drive system to effect a discharge of fluid from the canister into the piston chamber to drive the piston through the chamber. In an alternative embodiment, a manual drive system can be provided which includes a pivoting actuation handle associated with said handle portion and operatively connected to an elongated drive shaft which extends to the actuator.

Further features of the surgical apparatus will become more readily apparent to those skilled in the an from the following detailed description taken in conjunction with the drawings.

BRIEF DESCRIPTION OF THE DRAWINGS

Preferred embodiments of the surgical apparatus will be described hereinbelow with reference to the drawings wherein.

DETAILED DESCRIPTION OF PREFERRED EMBODIMENTS

Figure 1:
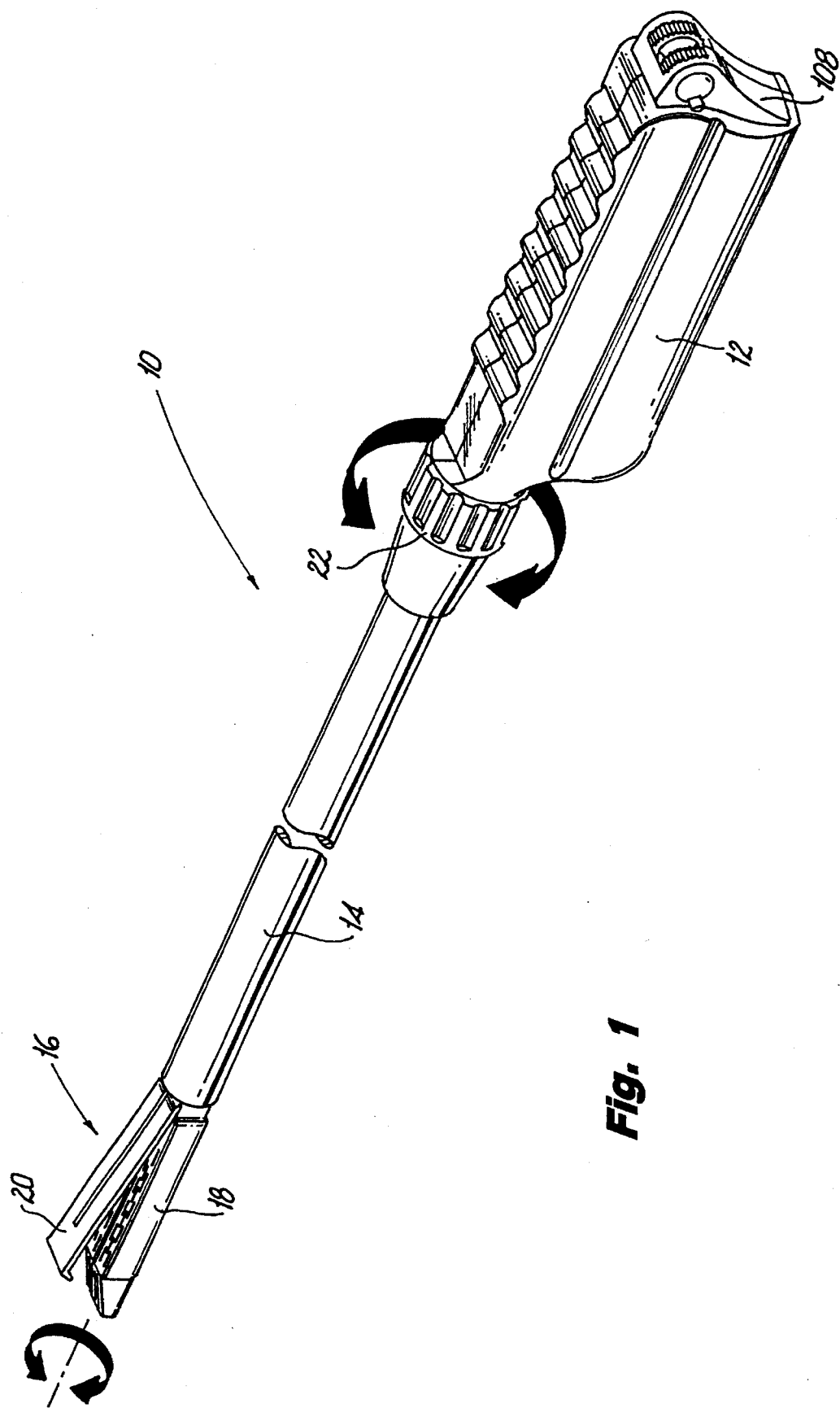
FIG. 1 is a perspective view of a surgical stapling apparatus constructed in accordance with a preferred embodiment.

In the drawings and in the description which follows, the term "proximal", as is traditional, will refer to the end of the apparatus which is closest to the operator, while the term "distal" will refer to the end of the apparatus which is furthest from the operator.

The present apparatus shall be discussed in terms of both endoscopic procedures and apparatus. However, use herein of terms such as "endoscopic", "endoscopically", and "endoscopic portion", among others, should not be construed to limit the apparatus for use only in conjunction with an endoscopic tube. To the contrary, it is believed that the apparatus may find use in procedures wherein access is limited to a small incision including but not limited to arthroscopic and/or laparoscopic procedures.

Referring now to the drawings wherein like reference numerals identify similar structural elements, there is illustrated in FIG. 1 a surgical stapler constructed in accordance with a preferred embodiment and designated generally by reference numeral 10. In brief, surgical stapler 10 includes a handle portion 12, an elongate tubular body portion 14 extending distally from handle portion 12, and a fastener applying assembly 16 operatively associated with a distal end of body portion 14.

Figure 1A:
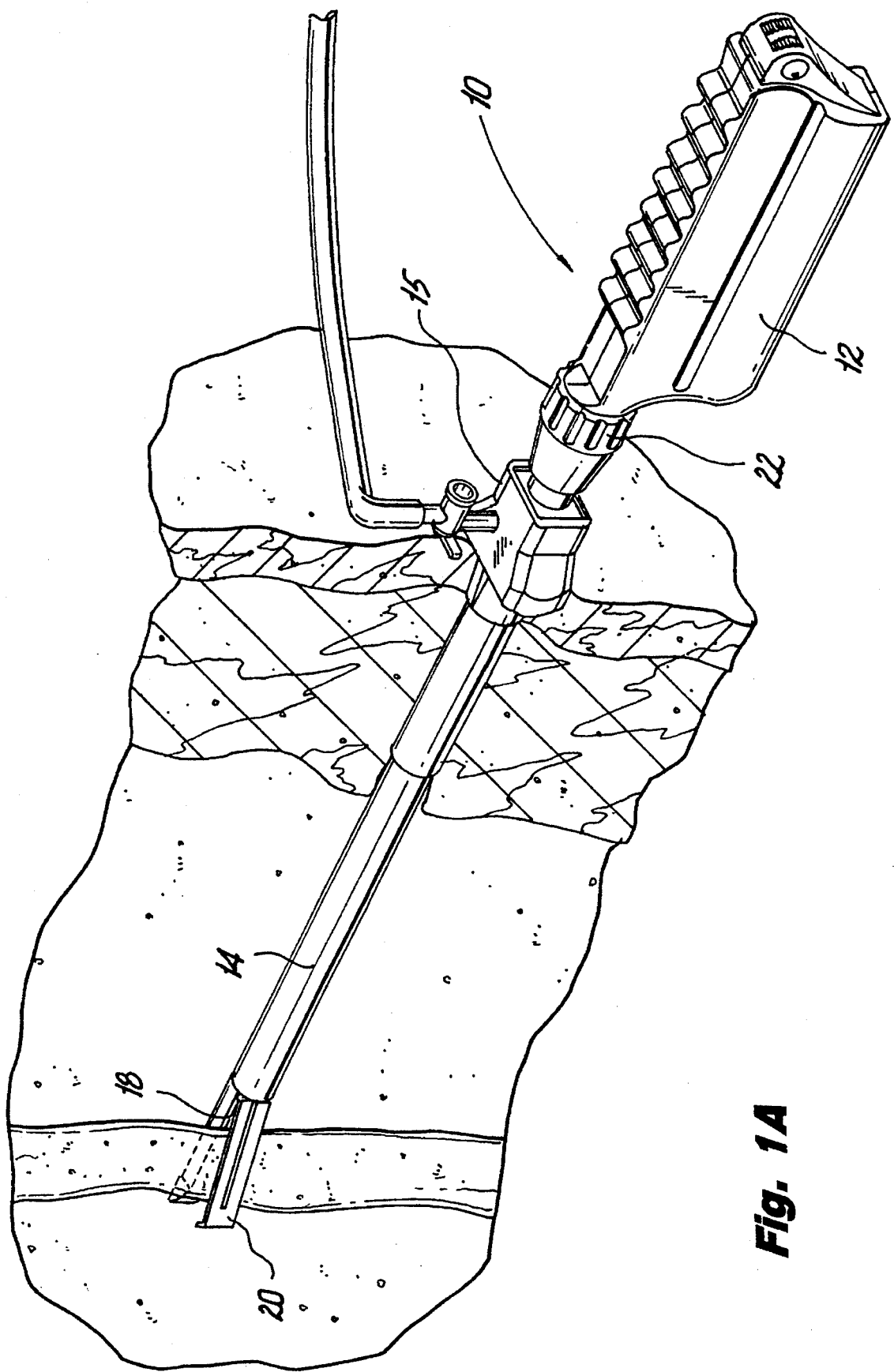
FIG. 1A is a perspective view of the surgical apparatus of FIG. 1 extending through a trocar into the abdominal cavity of patient to staple body tissue.

Fastener applying assembly 16 includes a staple cartridge 18 housing a plurality of surgical fasteners and an anvil member 20 pivotably associated with the staple cartridge and defining a forming surface against which staples are driven when ejected from cartridge 18. As best seen in FIG. 1, a rotation control knob 22 is provided at the proximal end of body portion 14 and is mounted in such a manner so as to facilitate rotation of body portion 14 and fastener applying assembly 16 about a longitudinal axis defined by the body portion 14. As illustrated in FIG. 1A, during an endoscopic procedure, the body portion 14 of surgical apparatus 10 is extended through a trocar 15 into the abdominal cavity of a patient. Thereupon, tissue is captured between cartridge 18 and anvil 20, and staples are applied to the tissue. The operation of surgical apparatus 10 will be discussed in detail hereinbelow.

Figure 2:
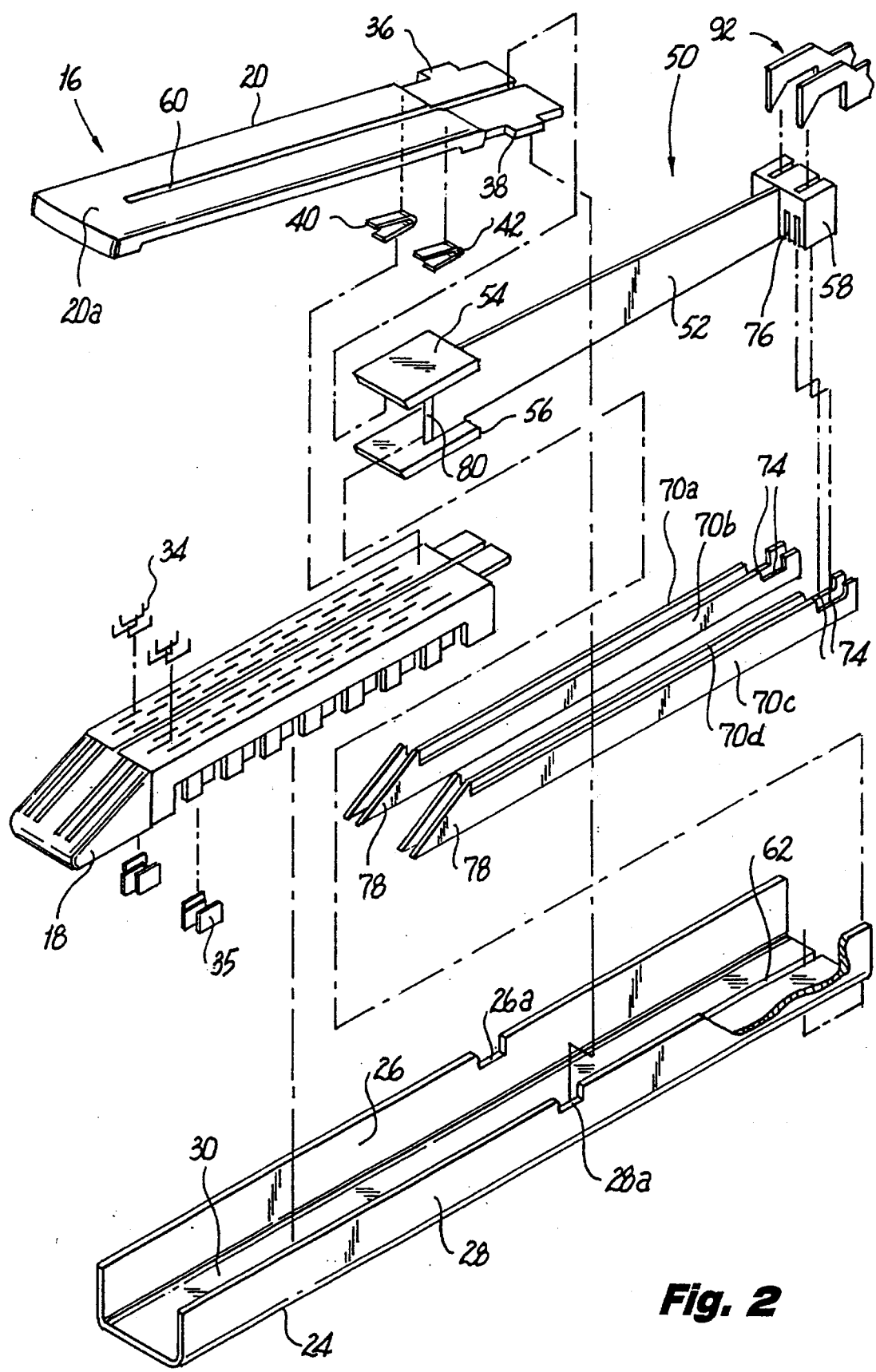
FIG. 2 is an exploded perspective view of the fastener applying assembly of the surgical apparatus illustrated in FIG. 1.
Figure 3:
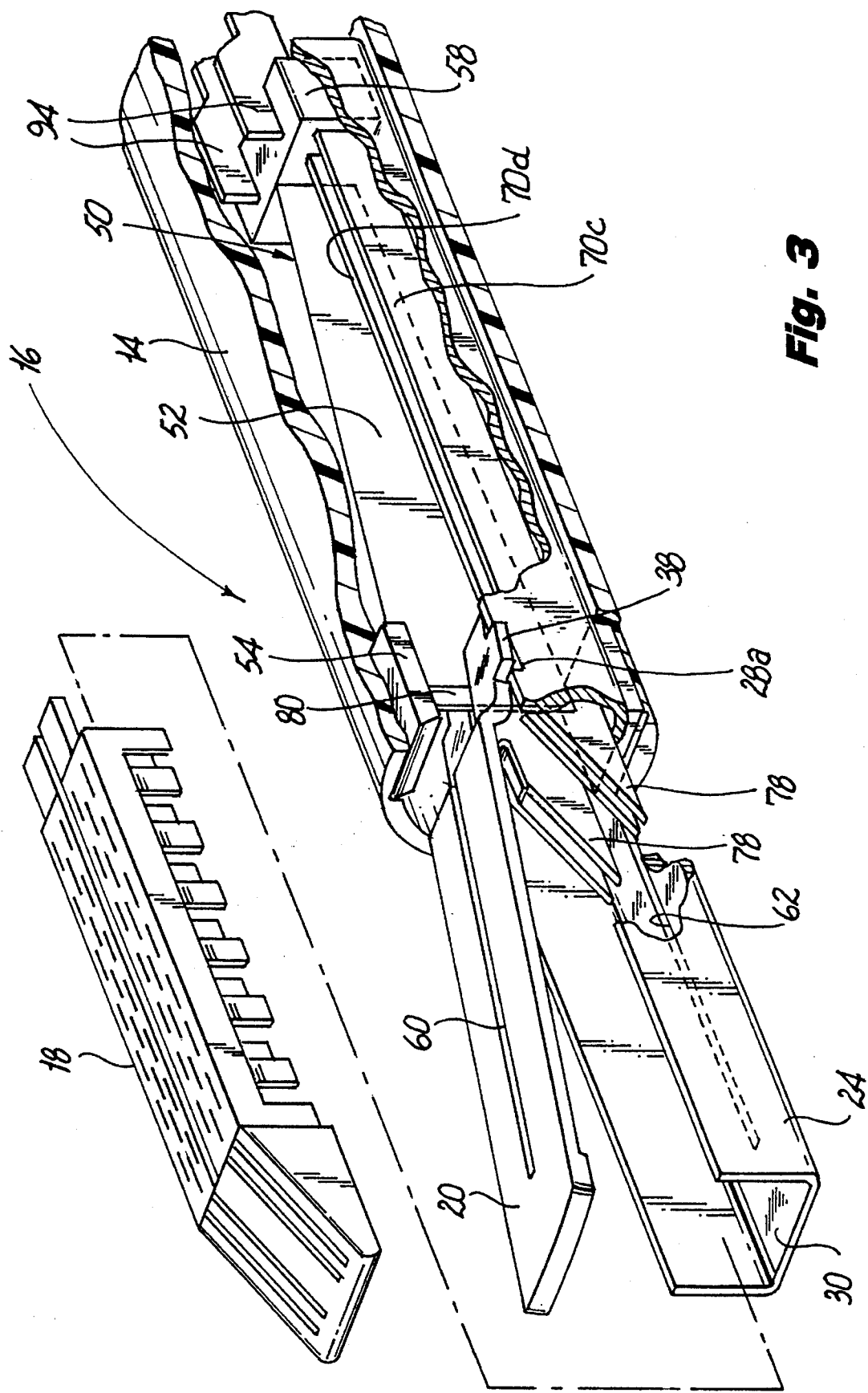
FIG. 3 is a perspective view of the fastener applying assembly of the surgical apparatus of FIG. 1, with the cartridge removed from the cartridge housing to illustrate the actuating structure of the instrument.
Figure 4:
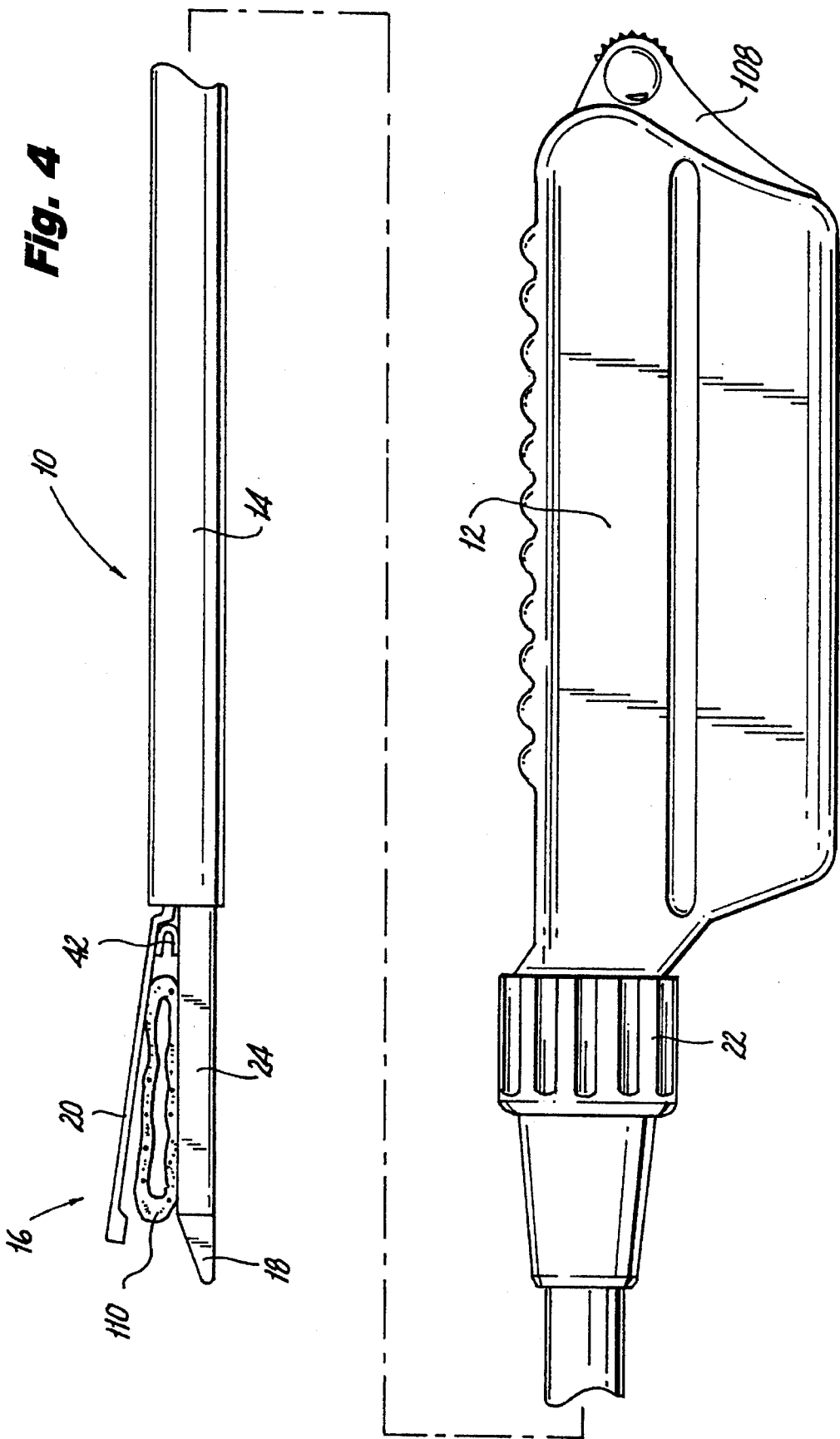
FIG. 4 is a side elevational view of the surgical apparatus of FIG. 1 prior to a staple applying operation.

Referring to FIG. 2, staple cartridge 18 is supported within an elongated cartridge housing 24 having opposed side walls 26 and 28 and a floor 30. As best seen in FIG. 3, cartridge housing 24 is supported in the distal end of body portion 14. Notches 26a and 28a are formed in side walls 26 and 28 respectively, for pivotably supporting a pair of corresponding winglets 36 and 38 which extend outwardly from anvil member 20. As shown in FIGS. 2 and 4, springs 40 and 42 are associated with anvil member 20 to bias the anvil into an open position with respect to cartridge 18. In an alternate embodiment, anvil member 20 can be directly attached to the body portion 14. In either embodiment, anvil member 20 is positioned distally of handle portion, and the fastener firing assembly is remotely actuated by the handle portion.

Alternately, a spring could be provided to bias the anvil to a closed position. The spring could extend, for example, from the proximal portion of anvil member 20 and be connected to body portion 14 or housing 24. Body tissue, when inserted between the anvil and cartridge would move the anvil away from the cartridge 18. The anvil would then be loosely clamped on the tissue until the actuation mechanism described below is actuated to more firmly and progressively clamp the tissue as the fasteners are fired.

Referring to FIGS. 2 and 3, an actuation mechanism 50 is associated with fastener applying assembly 16 to effectuate the progressive approximation of anvil 20 and cartridge 18 to clamp tissue therebetween, and concomitantly effect the sequential ejection of a plurality of surgical staples 34 from cartridge 18. More particularly, actuation mechanism 50 is configured to translate through fastener applying assembly 16, i.e. through anvil member 20 and cartridge 18, in a distal direction, to gradually cam anvil member 20 into a closed (or fully clamped) position and, at the same time, activate a plurality of staple drivers 35 to urge staples 34 from cartridge 18. An example of a suitable staple driver is disclosed in commonly assigned U.S. Pat. No. 4,978,049, the disclosure of which is herein incorporated by reference.

Actuation mechanism 50 includes an elongated support beam 52 having upper and lower cam plates 54 and 56 disposed at the distal end thereof, and a mounting block 58 disposed at the proximal end thereof. An elongate slot 60 is formed in anvil member 20 to accommodate the translation of actuation mechanism 50 during a stapling procedure. A corresponding slot 62 is formed in the floor 30 of cartridge housing 24. In use, when actuation mechanism 50 translates through fastener applying assembly 16, the upper cam plate 54 engages the upper (outer) surface 20a of anvil member 20 to urge it toward cartridge 18, and the lower cam plate 56 engages the under (outer) surface 30a of floor 30 to balance the compressive forces imparted on the anvil by the upper cam plate. As shown, the upper and lower cam plates 54, 56 are substantially planar.

Actuation mechanism 50 further includes staple firing bars 70a–70d configured to activate staple drivers 35. The firing bars are engaged to mounting block 58 at their respective proximal ends by an engagement hook 74 which is received in a corresponding engagement slot 76. The distal ends of each of the firing bars includes a wedged cam surface 78 which engages staple pushers 35 as actuation mechanism 50 translates through fastener applying assembly 16. The leading edge of support beam 52 defines a cutting blade 80 which is configured to form an incision in the tissue located between the parallel rows of staples applied by assembly 16.

Figure 5:
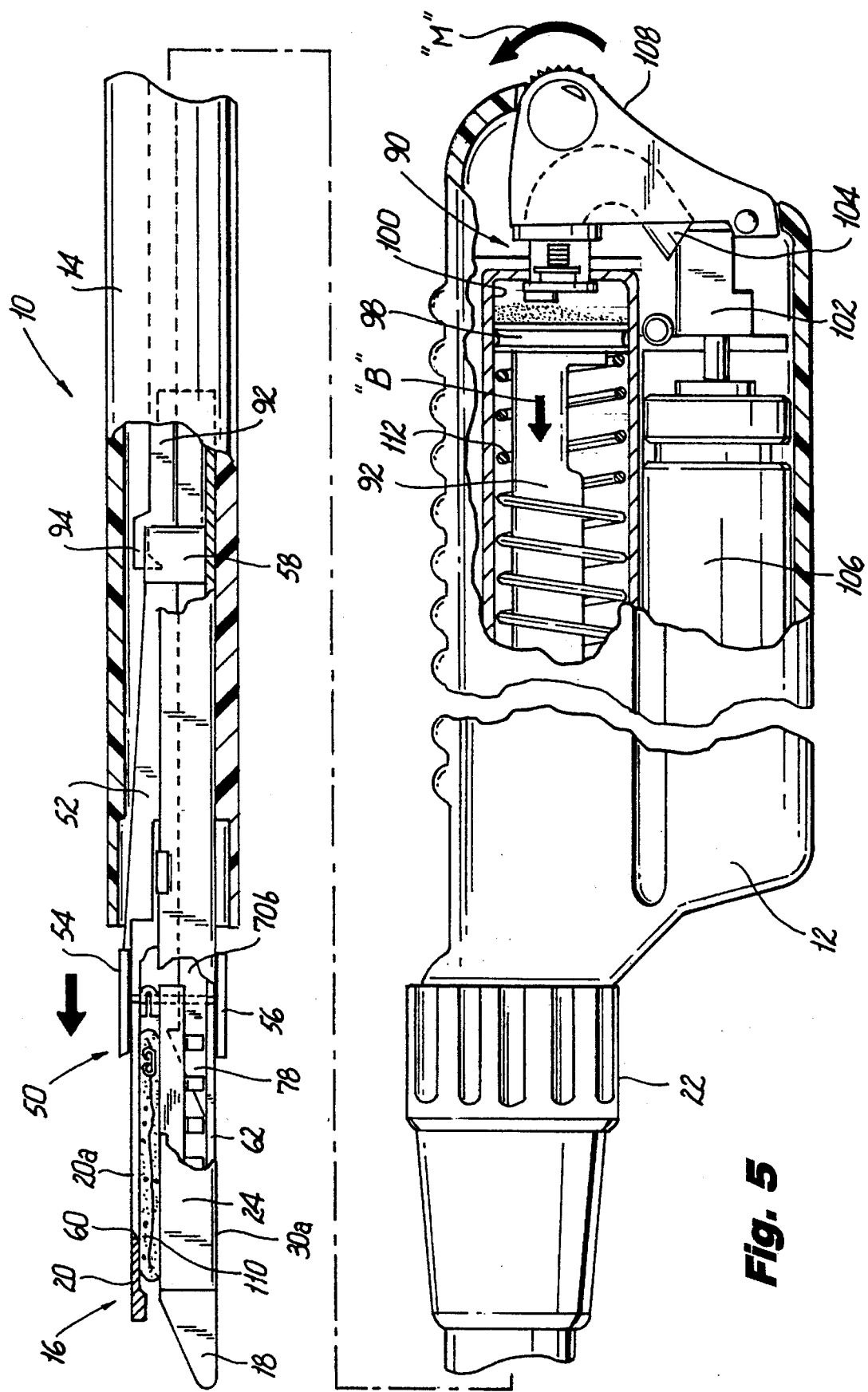
FIG. 5 is a side elevational view in partial cross-section of the apparatus of FIG. 1 during the initial stages of a staple applying operation.

Referring to FIG. 5, a pneumatic drive system 90 is operatively associated with handle portion 12 to control the translation of actuation mechanism 50 through fastener applying assembly 16 during a stapling procedure. In particular, drive system 90 serves to effect the longitudinal movement of a drive shaft 92 which extends from handle portion 12, through body portion 14, to fastener applying assembly 16. The distal end of drive shaft 92 includes a bifurcated hook portion 94 configured to engage corresponding reception slots 96a and 96b in mounting block 58 (see also, FIGS. 2 and 3).

The proximal end of drive shaft 92 extends from a piston 98. Piston 98 is configured to translate through an elongate piston chamber 100 which is defined within handle portion 12. Piston chamber 100 is in communication with a valve assembly 102 through a flexible conduit 104. Valve assembly 102 is associated with a cylindrical canister 106 containing a supply of relatively low pressure compressed gas. A pivoting trigger 108 is associated with handle portion 112 and is configured to interact with valve assembly 102 to control the emission of gas from supply canister 106 into piston chamber 100. The structure and operation of the pneumatic system is described in detail in commonly assigned U.S. Pat. No. 5,312,023, the disclosure of which is herein incorporated by reference.

In operation, as illustrated in FIG. 5, upon manipulation of trigger 108 in the direction indicated by arrow "A", valve assembly 102 causes compressed gas to flow from canister 106, through conduit 104, and into piston chamber 100. As a result of the expansion of the compressed gas within chamber 100, piston 98 is driven in a distal direction, as indicated by reference arrow "B". At such a time, drive shaft 92 is urged distally, driving actuation mechanism 50 into fastener applying assembly 16. The distal translation of actuation mechanism 50 causes cam plate 54 to urge anvil member 20 toward cartridge 18 to bring the fastener forming surface of anvil member 20 into closer cooperative alignment with the tissue contacting surface of cartridge 18, clamping the body tissue 110 disposed therebetween. Concomitantly, staple drivers 35 are activated by the wedged cam surface 78 on each of the staple firing bars 70a–70d, driving staples 34 through the captured body tissue 110. In addition, cutting blade 80 travels behind the staple firing bars to incise the stapled tissue.

Figure 6:
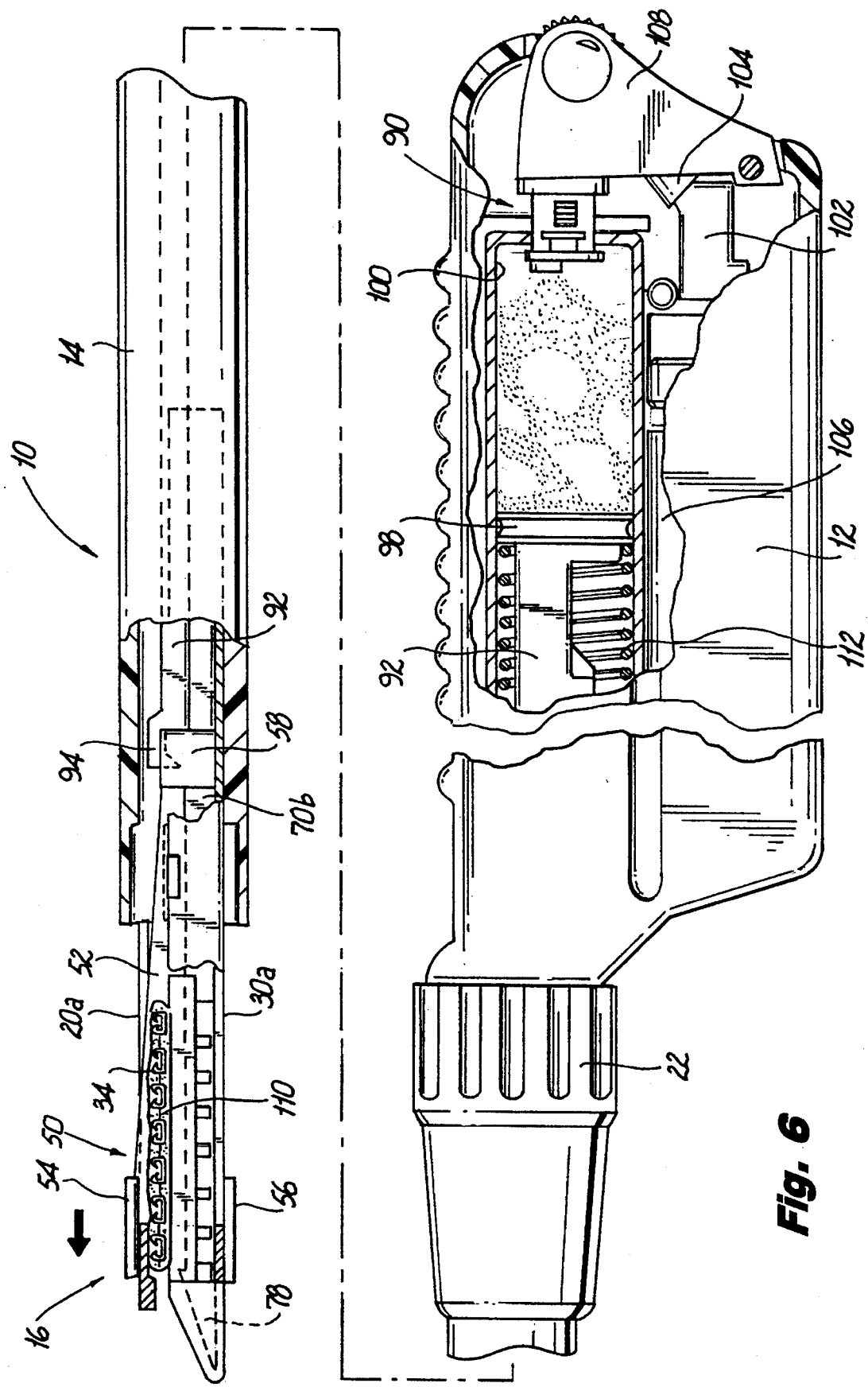
FIG. 6 is a side elevational view in partial cross-section of the apparatus of FIG. 1 at the conclusion of a staple applying operation.

As illustrated in FIG. 6, the expansion of compressed gas within piston chamber 100, causes piston 98 and actuation mechanism 50 to translate distally until each of the staples are ejected from the cartridge 18. Thereafter, a coiled return spring 112 disposed within piston chamber 100 and compressed by the distal movement of piston 98, biases the piston proximally, forcing the drive shaft 92 and actuation mechanism 50 to return to their distalmost positions. Thereupon, the spent staple cartridge can be removed from cartridge housing 24 and replaced with a fully loaded cartridge, and apparatus 10 can be utilized once again.

Although the subject apparatus has been described with respect to preferred embodiments, it will be readily apparent to those having ordinary skill in the art to which it appertains that changes and modifications may be made thereto without departing from the spirit or scope as defined by the appended claims.

What is claimed is:

1. An apparatus for applying surgical fasteners to body tissue comprising:
    a) a handle portion;
    b) a body portion extending distally from the handle portion;
    c) a cartridge housing supported in a distal end portion of the body portion and defining a tissue contacting surface the cartridge housing containing a plurality of surgical fasteners;
    d) an anvil member defining a fastener forming surface against which fasteners ejected from the cartridge housing are driven, the anvil member movably mounted for movement with respect to the cartridge housing at a location spaced from the handle portion, the anvil member movable between a first position and a second position wherein the fastener forming surface and the tissue contacting surface are in closer cooperative alignment;
    e) an actuation mechanism configured to translate through the anvil member and cartridge housing to progressively move the anvil member from the first position to the second position and concomitantly eject a plurality of surgical fasteners from the cartridge to be formed against the anvil; and
    f) a drive mechanism operable from the handle portion and extending through the body portion to drive the actuation mechanism through the anvil member.

2. An apparatus as recited in claim 1, wherein the cartridge housing and the anvil member each have a corresponding longitudinally extending slot formed therein for accommodating the translation of the actuation mechanism.

3. An apparatus as recited in claim 1, wherein the actuation mechanism includes an upper cam beam, a central portion, and a lower support beam parallel to the upper cam beam.

4. An apparatus as recited in claim 1, wherein the actuation mechanism includes a plurality of spaced apart cam bars configured to engage a plurality of staple pushers disposed within the cartridge housing to effect the ejection of surgical fasteners therefrom.

5. An apparatus as recited in claim 1, wherein the drive mechanism includes a pneumatic drive system associated with the handle portion and including a canister of compressed fluid disposed within the handle portion, a longitudinally extending piston chamber defined in the handle portion, a piston configured to translate through the piston chamber, and a drive shaft extending from the piston to the actuator.

6. An apparatus as recited in claim 5, further comprising a trigger mechanism associated with the pneumatic drive system to effect a discharge of fluid from the canister into the piston chamber to drive the piston through the chamber.

7. An apparatus as recited in claim 5, wherein the piston is configured to translate through the piston chamber in a generally distal direction.

8. An apparatus as recited in claim 7, further comprising a coiled return spring disposed within the piston chamber to bias the piston in a proximal direction.

9. An apparatus as recited in claim 1, further comprising a cutting blade mounted on the actuation mechanism for incising stapled tissue as the actuation mechanism translates through the anvil member and cartridge housing.

10. An apparatus as recited in claim 3, wherein a cutting blade is formed on a leading edge of the central portion of the actuator for incising stapled tissue as the actuation mechanism translates through the anvil member and cartridge housing.

11. An apparatus as recited in claim 1, wherein the anvil member is spring biased to the second position.

12. An apparatus as recited in claim 1, wherein the actuation mechanism includes upper and lower cam plates at a distal end and a mounting block at a proximal end to receive at least one fastener firing bar.

13. An apparatus as recited in claim 1, wherein the anvil member has an outer surface portion opposing the fastener forming surface and the actuation mechanism engages the outer surface portion.

14. An apparatus as recited in claim 13, wherein the anvil member includes a longitudinally extending slot and said actuation mechanism extends through said slot to engage said outer surface portion.

15. An apparatus as recited in claim 14, wherein said actuation mechanism includes a camming plate at a distal end to engage said outer surface portion of said anvil member.

16. An apparatus as recited in claim 15, wherein said cartridge housing includes an outer surface portion opposite the tissue contacting surface and a longitudinally extending slot, said actuation mechanism extending through said slot to engage said outer surface portion of said cartridge housing.

17. An apparatus as recited in claim 16, wherein said actuation mechanism includes a camming plate at a distal end to engage the outer surface portion of said cartridge housing.

18. An apparatus as recited in claim 17, wherein the camming plates for engaging the anvil member and the cartridge housing are substantially planar.

19. An apparatus as recited in claim 1, wherein the anvil member is spring biased to the first position.

20. An apparatus for applying surgical fasteners to body tissue comprising:
   a) a handle assembly;
   b) an elongated body portion extending distally from the handle portion and defining a longitudinal axis;
   c) a fastener applying assembly supported in a distal end portion of the body portion and including:
      1) a cartridge housing containing a plurality of surgical fasteners and defining a tissue contacting surface; and
      2) an anvil member defining a fastener forming surface against which fasteners ejected from the cartridge housing are driven, the anvil member mounted at a location distal of the handle assembly for movement between a first position and a second position wherein the fastener forming surface and the tissue contacting surface are in closer cooperative alignment;
   d) an actuator configured to translate through the fastener applying assembly in a generally distal direction to progressively move the anvil member from the first position to the second position and concomitantly eject a plurality of surgical fasteners from the cartridge housing to be formed against the fastener forming surface of the anvil member, and
   e) a pneumatic drive system operatively associated with the handle assembly and operable to drive the actuator through the fastener applying assembly.

21. An apparatus as recited in claim 20, wherein the actuator includes an upper cam beam, a central portion, and a lower support beam parallel to the upper cam 22. An apparatus as recited in claim 20, wherein the anvil member is spring biased to the first position.

23. An apparatus as recited in claim 21, wherein the cartridge housing and the anvil member each have a corresponding longitudinally extending slot formed therein for accommodating the translation of the actuator.

24. An apparatus as recited in claim 23, wherein the actuator includes a plurality of spaced apart cam bars configured to engage a plurality of staple pushers disposed within the cartridge housing to effect the ejection of surgical fasteners therefrom.

25. An apparatus for applying surgical fasteners to body tissue comprising:
   a) a handle portion;
   b) a body portion extending from the handle portion and defining a longitudinal axis;
   c) a cartridge housing containing a plurality of surgical fasteners mounted in a distal portion of the body portion;
   d) an anvil member against which fasteners ejected from the cartridge housing are driven, the anvil member having a fastener forming surface and an opposing external camming surface defined thereon, the anvil member and the cartridge housing mounted for relative movement between an open position and a closed position;
   e) an actuator configured to translate through the anvil member while contacting the external camming surface of the anvil member to progressively approximate the anvil member and the cartridge housing and concomitantly eject a plurality of surgical fasteners from the cartridge housing to be formed against the anvil; and
   f) a drive mechanism operable from the handle portion and extending through the body portion to drive the actuator through the anvil member.

26. An apparatus as recited in claim 25, wherein the drive mechanism includes a pneumatic drive system associated with the handle portion and including a canister of compressed fluid disposed within the handle portion, a longitudinally extending piston chamber defined in the handle portion, a piston configured to translate through the piston chamber, and a drive shaft extending from the piston to the actuator.

27. An apparatus as recited in claim 25, wherein the anvil member includes a longitudinally extending slot configured to receive the actuator.

28. An apparatus as recited in claim 27, wherein the cartridge housing includes a longitudinally extending slot configured to receive the actuator.

* * * * *